United States Patent [19]
Stevens

[11] Patent Number: 5,616,203
[45] Date of Patent: Apr. 1, 1997

[54] METHOD OF MANUFACTURING A SPLIT RING AIRLESS ROTATABLE CONNECTOR

[75] Inventor: Brian Stevens, Pleasant Grove, Utah

[73] Assignee: Merit Medical, South Jordan, Utah

[21] Appl. No.: 502,754

[22] Filed: Jul. 14, 1995

[51] Int. Cl.[6] ..................................................... F16L 27/08
[52] U.S. Cl. .......................... 156/91; 156/273.7; 156/293; 285/281
[58] Field of Search ...................................... 285/281, 276; 156/293, 273.7; 186/91

[56] References Cited

U.S. PATENT DOCUMENTS

| | | | |
|---|---|---|---|
| 2,833,568 | 5/1958 | Corsette | 285/281 |
| 4,932,114 | 6/1990 | Morse et al. | 29/443 |
| 5,060,987 | 10/1991 | Miller | 285/328 |
| 5,078,433 | 1/1992 | Morse et al. | 285/281 |
| 5,167,636 | 12/1992 | Clement | 604/167 |
| 5,197,463 | 3/1993 | Jeshuran | 128/207 |
| 5,299,843 | 4/1994 | Weigl et al. | 285/328 |
| 5,324,271 | 6/1994 | Abiuso et al. | 604/167 |
| 5,350,205 | 9/1994 | Aldridge et al. | 285/328 |

OTHER PUBLICATIONS

Product catalog of Merit Medical which illustrates and describes a Y adapter featuring an airless rotator to eliminate bubbles, 1994.

Product catalog of Braun which illustrates and describes various Braun Y-Connectors, Sep. 1993.

Product catalog of Cook Cardiology, a division of Cook Incorporated which, illustrates and describes the Large Bore Tuohy-Borst Side-Arm Adapter, 1992.

*Primary Examiner*—Michael W. Ball
*Assistant Examiner*—Sam Chuan Yao
*Attorney, Agent, or Firm*—Workman Nydegger Seeley

[57] ABSTRACT

A rotatable connector having an enlarged annular flange positioned at the distal end of a tubular body. An annular cap having an aperture is received on the tubular body through the aperture so as to rotatably encircle the tubular body proximal of the retaining flange. A split ring rotatably encircles the tubular body between the retaining flange and the cap. The split ring has an inner diameter smaller than the outer diameter of the retaining flange and an outer diameter larger than the inner diameter of the aperture of the cap. An access chamber positioned at the proximal end of a tubular hub receives the distal end of the tubular body in mating relationship to enable the proximal end of the hub to be ridgedly coupled to the cap. A transfer duct communicating with the access chamber in the tubular hub is rotatably fluid coupled with the passage in the tubular body.

26 Claims, 11 Drawing Sheets

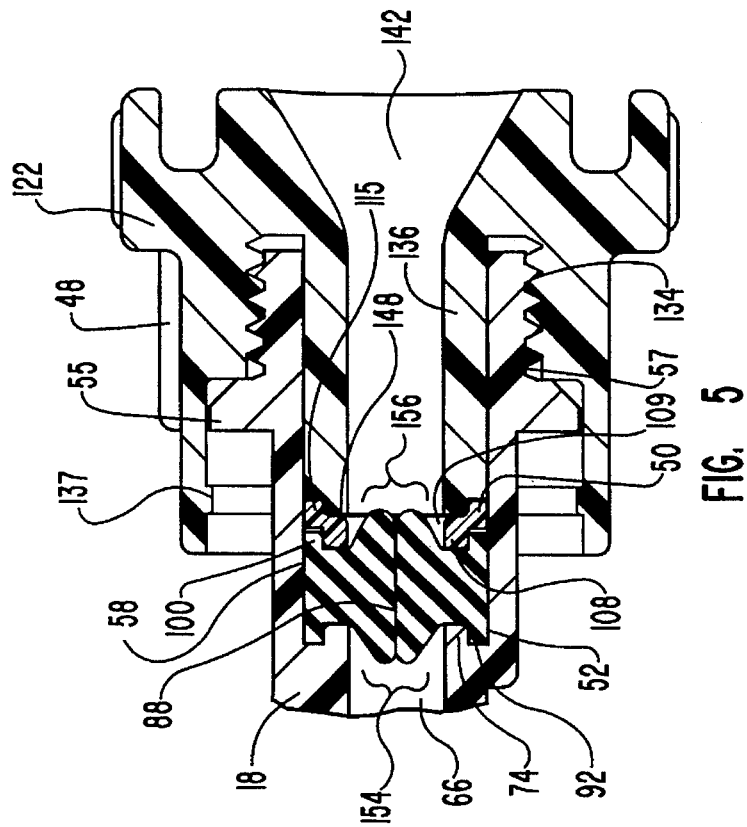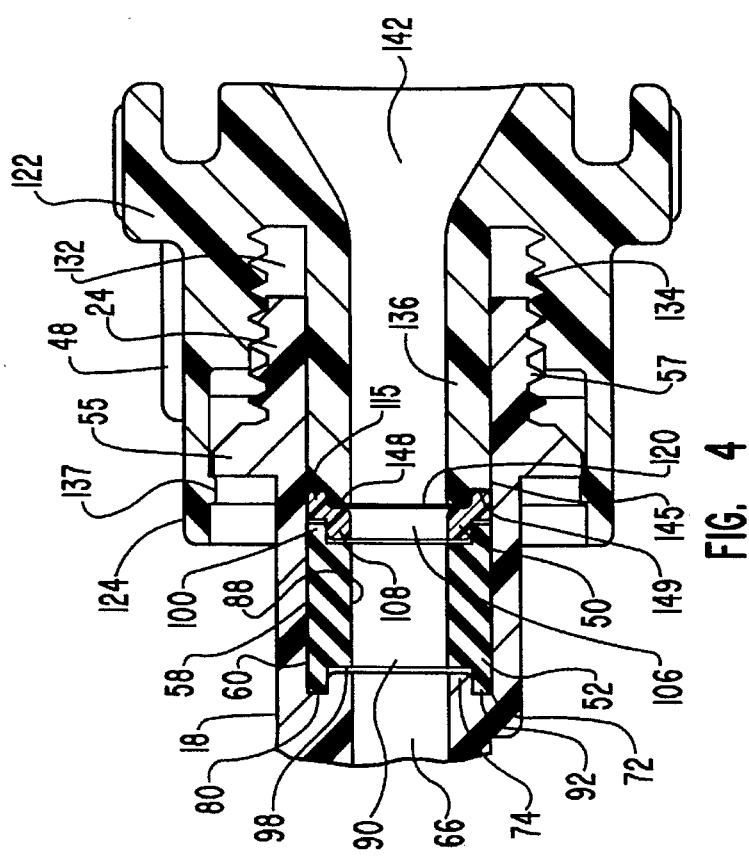

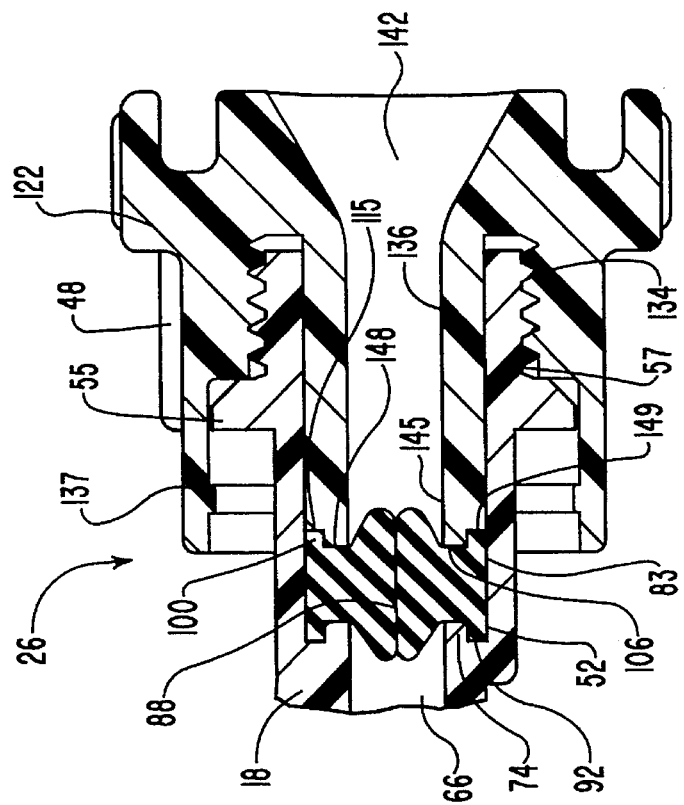
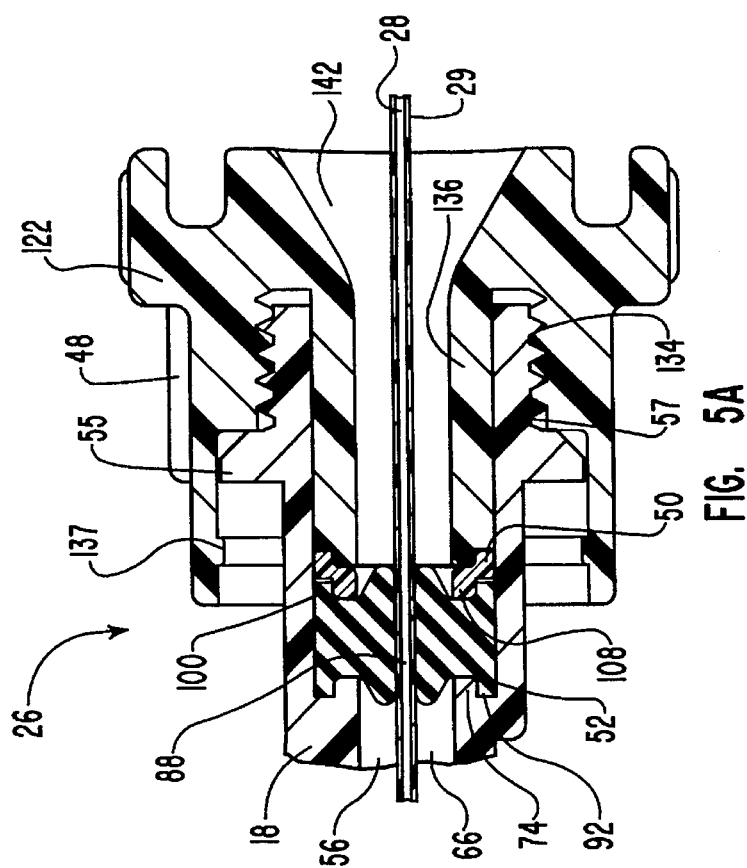
FIG. 5B
FIG. 5A

METHOD OF MANUFACTURING A SPLIT RING AIRLESS ROTATABLE CONNECTOR

SUMMARY OF THE INVENTION

1. The Field of the Invention

The present invention relates to methods for manufacturing rotatable connectors and, more specifically, to methods for manufacturing rotatable connectors used for attachment to a medical device in fluid communication with the body of a patient

2. The Relevant Technology

Several modern surgical procedures require temporary and often repeated introduction and removal of catheters and/or guidewires within the cardiovascular system of a patient. For example, using only a relatively small incision, a catheter can be introduced into the body of a patient and used to deliver fluid, such as medication, directly to a predetermined location within the cardiovascular system. Catheters can also be used for exploratory surgery and for removing tissue samples within a body. One increasingly common use for catheters is in the placement of small balloons which can be selectively inflated within a blood vessel. The balloons are used for opening blood vessels that have been blocked or partially blocked by fat build-up. This opening or altering of the vein is referred to as angioplasty.

A common catheter design used in performing many of the procedures mentioned above includes an elongated, flexible, cylindrical catheter body having a fluid flow passageway or a lumen extending along the interior of that catheter body. During one type of use, an end of the catheter referred to as the distal end is inserted into the body of the patient through an incision in a blood vessel in the cardiovascular system. The distal end of the catheter is advanced along the internal passageway of the vessel until the distal end is located at a desired predetermined location for conducting an intended activity.

A guidewire is a long, cylindrical, flexible wire that is commonly used for directing the catheter to the desired location within the body. A guidewire is typically smaller in diameter and more rigid than a catheter. It is, therefore, easier for a surgeon to first direct and advance the guidewire within the cardiovascular system to the desired location within the body of the patient. The opposing end of the guidewire, positioned outside the body of the patient, is then received within the lumen of the catheter. Using the guidewire as a guide, the catheter is advanced along the length of the guidewire so as to properly position the catheter within the body of the patient. If desired, the guidewire can then be removed from within the catheter to open the lumen of the catheter. In an alternative process for inserting the catheter, the guidewire is initially received within the lumen of the catheter, and the catheter and guidewire are simultaneously advanced within the cardiovascular system of the patient.

Operations using catheters can often require the insertion and removal of several different types of catheters and guidewires. One of the problems encountered with the insertion and removal of catheters and guidewires is controlling bleeding at the point where the catheters and guidewires are first introduced into the cardiovascular system.

In one approach to controlling bleeding and insuring easy insertion and removal of a catheter and/or guidewire within the cardiovascular system, a distal end of an introducer is first secured within a large vein of a patient. An introducer is a relatively large, hollow tube. The opposite end of the introducer is positioned outside the body of the patient and is attached to an adapter.

An adapter typically comprises a short, rigid tube having a passageway extending therethrough. Attached at one end of the adapter tube, referred to as the distal end, is a connector. The connector is used to connect the passageway of the adapter to the exposed end of the introducer. This enables fluids and/or medical instruments, such as catheters and guidewires, to pass between the adapter and the introducer.

Positioned at the opposite end of the adapter tube, referred to as the proximal end, is a valve commonly referred to as a hemostasis valve. The hemostasis valve includes an enlarged chamber positioned at the proximal end of the adapter tube. The chamber is aligned with and is connected to the passageway extending through the adapter tube.

Positioned within the chamber is a soft, compressible seal. The seal has the appearance of a short piece of cylindrical tubing with a passage extending therethrough. The seal is oriented within the chamber so that the passage in the seal is aligned with and connected to the passageway in the adapter tube.

Finally, a rigid, hollow shaft is also positioned within the chamber. The hollow shaft has an entryway extending therethrough. The shaft is positioned so that the entryway in the shaft is aligned with and connected to the passage in the seal.

The shaft and seal are thus shaped and oriented so that an access is formed through the valve and into the passageway into the adapter tube. In this configuration, a catheter or guidewire can be inserted in the access in the valve and then advanced through the adapter, through the introducer, and into the cardiovascular system of the patient for desired positioning therein.

By advancing the shaft within the chamber, the seal compresses within the chamber. Compression of the seal causes the passage in the seal to constrict. If the shaft is advanced sufficiently far within the chamber, the passage in the seal constricts so as to compress and seal around the exterior surface of a catheter or guidewire positioned therein. Alternatively, if the catheter or guidewire is removed from within the seal, the passage in the seal can constrict so that the seal completely closes off the access through the valve.

During use of the adapter, the pressure on the patient's blood, caused by the beating of the patient's heart, causes the patient's blood to flow up through the introducer and into the passageway of the adapter tube. The seal, which is either independently closed or compressed around a catheter or guidewire, prevents the blood from spilling out of the adapter through the access in the valve.

The connector, positioned at the opposing end of the adapter, is preferably made rotatable about the adapter tube. In this way the connector can be rotated to screw onto the introducer or other medical device while the adapter is held stationary. Such connectors have previously been made by first sliding the distal end of the adapter tube through a hole in a circular plate so that the plate can rotatably encircle the distal end of the adapter tube. A second rigid tube having a flange or ring encircling the tube was then glued to the distal end of the adapter tube. The flange was larger than the hole in the plate and thus allowed the plate to rotate around the adapter tube but prevented the plate from sliding off the distal end of the adapter tube. The remaining portion of the connector, referred to as a hub, was then secured to the plate.

The hub, having threads for connection to a medical device, could then be rotated with the plate for attachment to a medical device.

The problem with this configuration is that gluing of the second tube onto the adapter tube could result in the glue seeping into the passageway in the adapter where the glue would harden. In turn, the hardened glue could create a rough surface on the interior of the passageway which could damage delicate instruments being advanced through the passageway. Furthermore, the insertion of catheters and other instruments could cause portions of the hardened glue to break off and enter the blood stream. Such particles are potentially harmful to the patient.

In an alternative approach to making a rotatable connector, the flange was initially molded on the distal end of the adapter tube. The hub was designed having a recess at one end. The flange on the adapter tube was inserted into the recess. The mouth of the recess was then heated and folded over behind the flange. In this configuration, the hub was again able to rotate freely relative to the adapter tube and was prevented from separation from the adapter tube by the interaction between the flange and the folded portion of the hub.

The problem with this approach, however, is that heating of the leading edge of the hub for folding is a relatively lengthy, time consuming process. Furthermore, the process requires expensive equipment to heat and fold over the right proportion of the hub.

Further still, the interaction between the hub and the flange is often difficult to control and thus had a high variability in how easily the hub rotated relative to the tubular member.

OBJECTS AND SUMMARY OF THE INVENTION

Accordingly, it is an object of the present invention to provide methods for manufacturing improved rotatable connectors for attachment to medical devices.

It is another object of the present invention to provide improved methods for manufacturing rotatable connectors which can be manufactured without the risk of an adhesive forming a rough and potentially damaging surface on the interior of the passageway extending through the rotatable connectors.

Still another object of the present invention is to provide improved methods for manufacturing rotatable connectors which can be manufactured without the risk of cured adhesive particulate contaminating the blood stream of a patient.

Yet another object of the present invention is to provide improved methods for manufacturing rotatable connectors which can be manufactured relatively quickly.

Another object of the present invention is to provide methods for manufacturing rotatable connectors which can be manufactured without the use of expensive heating equipment used in heating and folding a portion of the rotatable connectors during assembly.

Finally, another object of the present invention is to provide improved methods for manufacturing rotatable connectors which have a desired ease of rotation.

These and other objects and features of the present invention will become more fully apparent from the following description and appended claims, or may be learned by the practice of the invention as set forth hereinafter.

To achieve the foregoing objects, and in accordance with the invention as embodied and broadly described herein, a method for manufacturing a rotatable connector is provided. The method includes the step of obtaining a tubular body having a distal end, an exterior surface, and an interior surface defining a passage longitudinally extending therethrough. The tubular body has an enlarged retaining flange positioned at the distal end extending radially outward from the exterior surface of the tubular body.

The distal end of the tubular body is advanced through an aperture in an annular cap until the cap is positioned proximal of the retaining flange. The annular cap comprises a cylindrical sleeve having a proximal end, a distal end, and an interior surface defining a recess. Furthermore, the annular cap has an annular end wall extending inward from the interior surface of the sleeve at the proximal end to define an aperture. The aperture has an inner diameter larger than the outer diameter of the retaining flange.

The next step includes positioning an expandable, annular split ring around the tubular body between the fastening cap and the retaining flange. The split ring has an interior surface encircling the tubular body. The interior surface defines an opening having an inner diameter smaller than the outer diameter of the retaining flange. The split ring also has an outer diameter larger than the inner diameter of the aperture of the cap.

Next, the distal end of the tubular body is received within an access chamber positioned at a proximal end of a tubular body. The access chamber has a proximal end, a distal end, and an inner diameter. Once the distal end of the tubular body is received within the access chamber, the passageway of the tubular body is rotatably fluid coupled with a transfer duct. The transfer duct communicates with the access chamber at the distal end of the access chamber. The transfer duct has an inner diameter smaller than the inner diameter of the access chamber so that an annular shoulder extends therebetween.

Finally, the proximal end of the hub is received within the recess of the cap and rigidly secured thereto. Securing the hub to the cap is preferably accomplished by applying an ultraviolet adhesive and then directing ultraviolet light onto the adhesive.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 4 is a cross-sectional view of the valve assembly shown in FIG. 3 in an assembled condition;

FIG. 5 is a cross-sectional view of the valve assembly shown in FIG. 4 and showing a seal positioned therein being compressed so as to seal the valve assembly;

FIG. 5A is a cross-sectional view of the valve assembly shown in FIG. 5 with the seal compressing and sealing around a catheter disposed therethrough;

FIG. 5B is a cross-sectional view of the valve assembly shown in FIG. 5 without the use of a slip ring positioned adjacent to the seal;

DETAILED DESCRIPTION OF THE PREFERRED EMBODIMENTS

Figure 1:
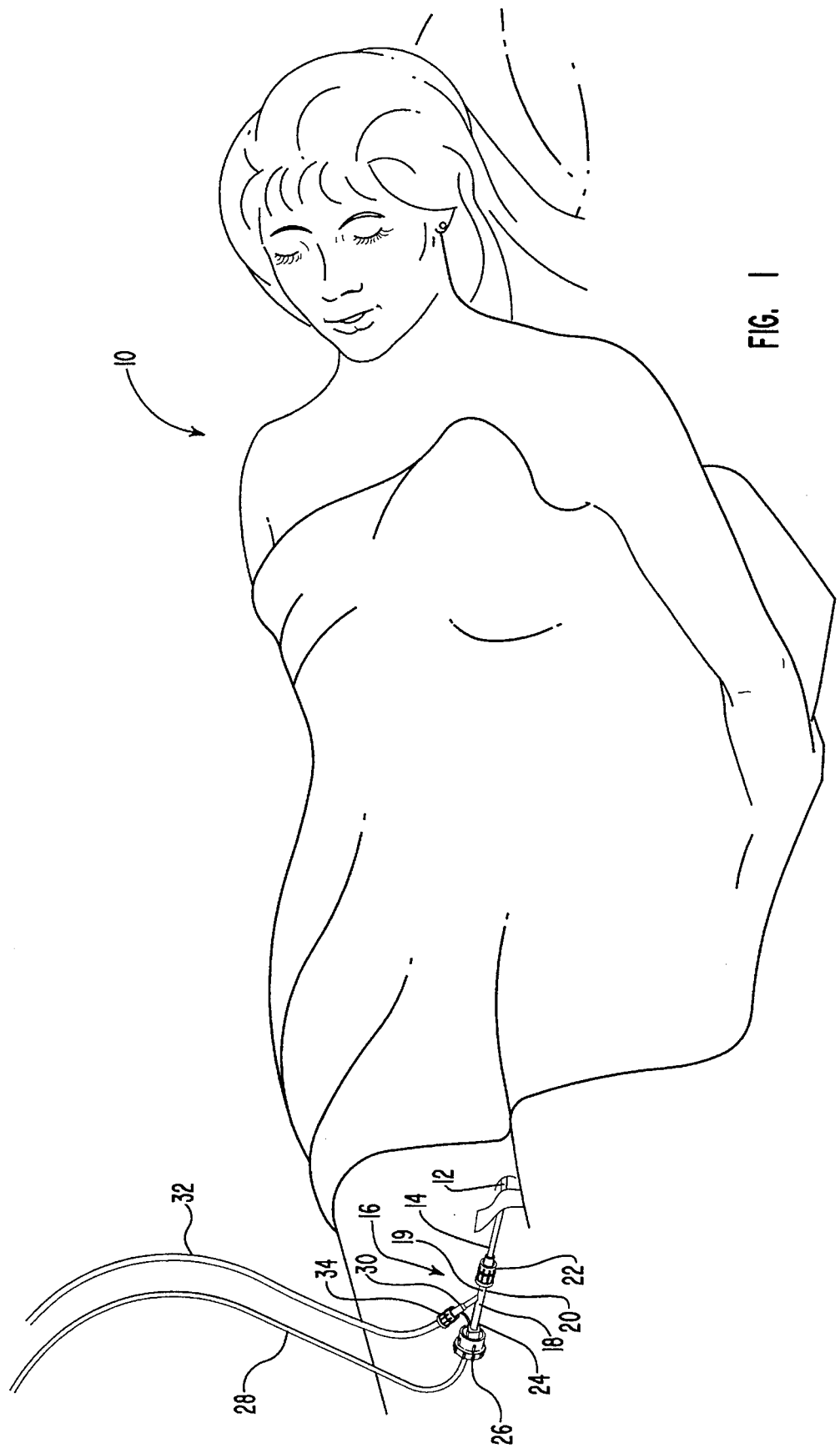
FIG. 1 is a perspective view of an adapter having a rotatable connector and a valve assembly and used for introducing a catheter into the cardiovascular system of a patient.

Referring to FIG. 1, a patient 10 is shown having an introducer 12 with a distal end (not shown) in fluid communication with the cardiovascular system of patient 10. A proximal end 14 of introducer 12 projects outside the body of patient 10 and is connected to one embodiment of an adapter 16 incorporating features of the present invention. Adapter 16 comprises a tubular body 18 having an exterior surface 19 with a distal end 20 and a proximal end 24 positioned at opposing ends thereof. A rotatable connector 22 is positioned at distal end 20. Rotatable connector 22 is shown in FIG. 1 as providing a fluid coupling between introducer 12 and tubular body 18.

Positioned at proximal and 24 is a valve assembly 26. As will be discussed later in greater detail, valve assembly 26 can be used to achieve alternative objectives. In one position, valve assembly 26 can be used to completely block off proximal end 24 of tubular body 18 so as to prevent the escape of blood or other bodily fluids flowing from patient 10, through introducer 12, and into adapter 16. Alternatively, valve assembly 26 can be used to form a seal around an elongated member 28, such as a catheter or guidewire, when elongated member 28 is received within valve assembly 26 and passed through tubular body 18, introducer 12, and into the cardiovascular system of patient 10. Valve assembly 26 thus also prevents the backflow of bodily fluids from introducer 12 from leaking out of adapter 16 where elongated member 28 is received within valve assembly 26.

Adapter 16 further comprises a supplemental access tube 30 in fluid communication with tubular body 18 between proximal end 24 and distal end 20. Supplemental access tube 30 is shown in fluid communication with a catheter 32 by way of a connector 34. In alternative embodiments, adapter 16 can have a plurality of supplemental access tubes communicating with tubular body 18. Supplemental access tube 30 can be used for introducing fluids or other medical devices into the body of patient 10.

Figure 2:
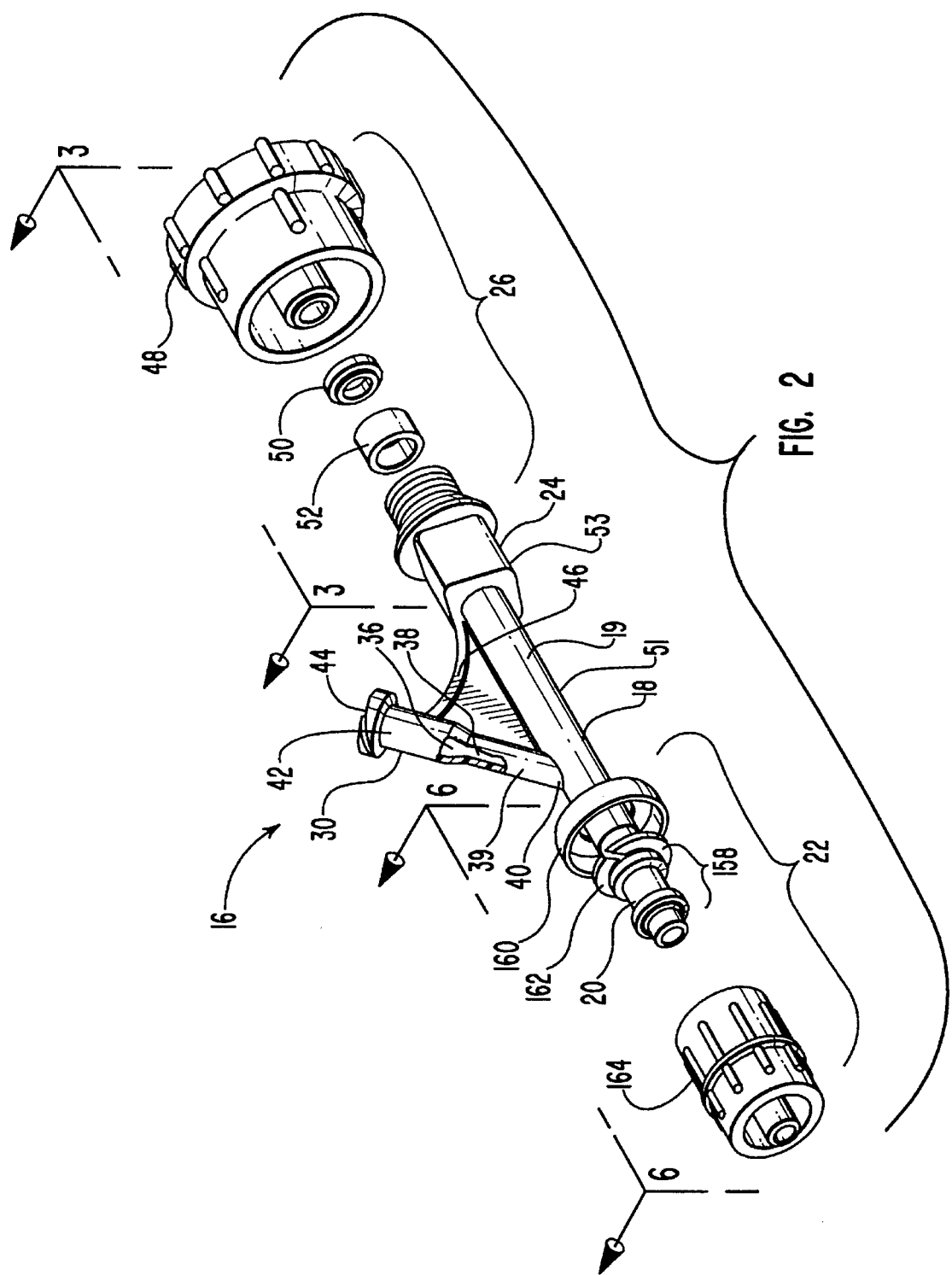
FIG. 2 is an enlarged perspective view of the adapter in FIG. 1 having the rotatable connector and valve assembly in a partially disassembled condition.

Depicted in FIG. 2 is a partially exploded or disassembled view of adapter 16. As disclosed therein, access tube 30 comprises an exterior surface 39 and an interior surface 36 defining a channel 38 longitudinally extending therethrough. Access tube 30 is attached in fluid communication at distal end 40 thereof to tubular body 18. Opposite distal end 40 is a free proximal end 42 having threads 44 positioned thereat. Threads 44 are preferably configured to accommodate a conventional luer lock attachment.

Access tube 30 is preferably positioned at an angle so as to project towards proximal end 24 of tubular body 18. A support member 46 extends between exterior surface 19 of tubular body 18 and exterior surface 39 of access tube 30. Support member 46 rigidly positions access tube 30 and helps to prevent fracture or breaking of access tube 30.

Figure 3:
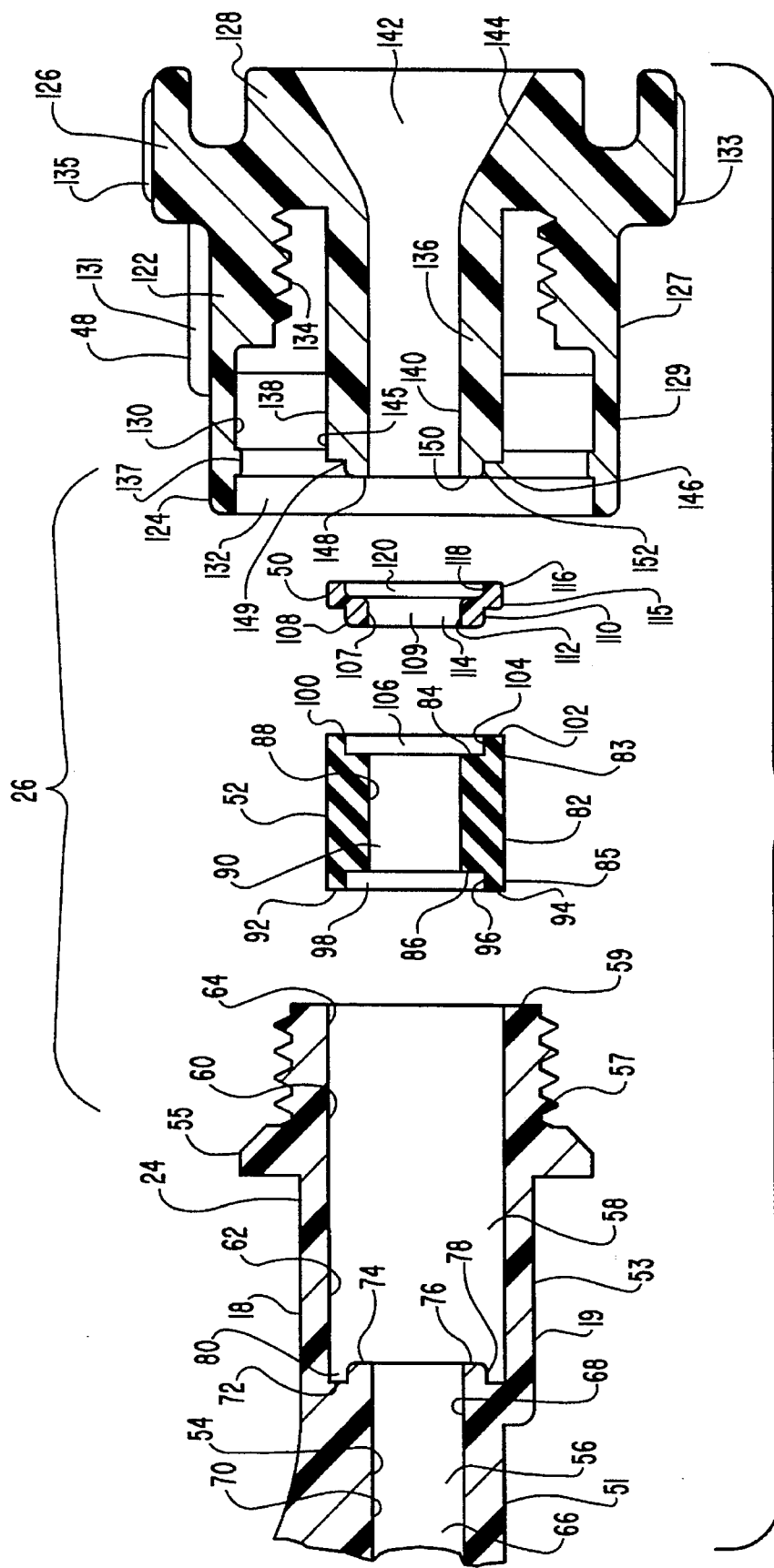
FIG. 3 is an enlarged cross-sectional view of the valve assembly shown in FIG. 2 in a disassembled condition.

Valve assembly 26 is depicted in FIG. 2 as further comprising a rotation nut 48, a slip ring 50, and a tubular seal 52. The configuration and interrelationship of these components are more clearly shown in FIG. 3 which discloses a cross-sectional exploded view of valve assembly 26. As depicted in FIG. 3, tubular body 18 has an interior surface 54 defining a passage 56 longitudinally extending through body 18. At proximal end 24, passage 56 is shown as comprising a compression chamber 58 positioned at a proximal terminus 59 of body 18. Compression chamber 58 has an inner diameter defined by an interior surface 60 extending between a distal end 62 and a proximal end 64.

Passage 56 further comprises a lumen 66 communicating at a proximal end 68 thereof to distal end 62 of compression chamber 58. Lumen 66 is concentric with compression chamber 58 and has an interior surface 70 having an inner diameter smaller than the inner diameter of compression chamber 58. Lumen 66 and compression chamber 58 are preferably substantially cylindrical.

An annular shoulder 72 extends between proximal end 68 of lumen 66 and distal end 62 of compression chamber 58. An annular first ridge 74 proximally projects from annular shoulder 72 and adjacently encircles lumen 66. First ridge 74 comprises an annular end face 76 and an annular sidewall 78. First ridge 74 has an outer diameter smaller than the inner diameter of compression chamber 58. As such, an annular first receiving groove 80 is formed between sidewall 78 of first ridge 74 and interior surface 60 of compression chamber 58.

As perhaps best seen in FIG. 2, exterior surface 19 of tubular body 18 includes a substantially cylindrical section 51 surrounding lumen 66 and a substantially rectangular casing 53 surrounding compression chamber 58. The configuration of rectangular casing 53 is to provide flat surfaces that enable medical personnel to clamp or use other mechanical means for holding adapter 16. Of course, rectangular casing 53 could be fashioned in alternative polygonal or circular cross-sectional configurations.

Returning again to FIG. 3, encircling body 18 at proximal end 24 and radially extending outward therefrom is a first compression lip 55. First compression lip 55 has an outer diameter and will be discussed later in greater detail. Positioned proximal of first compression lip 55 and also encircling body 18 are first engagement threads 57 which will also be discussed later in greater detail.

Tubular seal 52 is configured to mate within compression chamber 58. Tubular seal 52 has an exterior surface 82 extending between a proximal end 83 having a proximal end face 84 and a distal end 85 having a distal end face 86. Exterior surface 82 has an outer diameter approximately equal to the inner diameter of compression chamber 58 such that tubular seal 52 is received within compression chamber 58.

Seal 52 also has an interior surface 88 defining a passageway 90 longitudinally extending therethrough and axially aligned with lumen 66. An annular first tongue 92 distally projects from distal end face 86 and encircles passageway 90. First tongue 92 has an annular distal end face 94 and an annular interior sidewall 96. Interior sidewall 96 defines a first recess 98 concentric with passageway 90 and having an inner diameter greater than the inner diameter of passageway 90. As depicted in FIG. 4, which is an assembled view of the elements in FIG. 3, seal 52 is configured such that as seal 52 is mated within compression chamber 58, first tongue 92 is received within first receiving groove 80 and first ridge 74 is received within first recess 98.

Referring again to FIG. 3, an annular second tongue 100 proximally projects from proximal end face 84 of seal 52 and encircles passageway 90. Second tongue 100 comprises an annular proximal end face 102 and an annular interior sidewall 104. Interior sidewall 104 defines a second recess 106 concentric with passage 90 of seal 52 and having an inner diameter greater than the inner diameter of passage 90.

Slip ring 50 is depicted in FIG. 3 as having an interior surface 107 defining an opening 109 longitudinally extending through slip ring 50 and axially aligned with lumen 66. Slip ring 50 comprises a first ring 108 having an exterior surface 110 with an outer diameter and an interior surface 112 defining a first access 114. Proximally attached to first ring 108 is an annular second ring 115. Second ring 115 has an exterior surface 116 with an outer diameter greater than the outer diameter of first ring 108 and an interior surface 118 defining a second access 120. Second access 120 has an inner diameter greater than the inner diameter of first access 114. Second access 120 is concentric with first access 114 and communicates therewith to define opening 109.

As again shown in FIG. 4, slip ring 50 is configured such that in an assembled condition first ring 50 is received within second recess 106 of seal 52 while second tongue 100 of seal 52 encircles first ring 108.

As shown in FIG. 3, rotation nut 48 has a substantially cylindrical configuration and includes a housing 122 with a distal end 124 and an opposing proximal end 126. A proximal end wall 128 radially extends inward at proximal end 126. Housing 122 has an exterior surface 127 comprising a first cylindrical portion 129 positioned at distal end 124. A plurality of gripping ribs 131 radially extend outward on first cylindrical portion 129 and are aligned with the longitudinal access of body 18. Exterior surface 127 further comprises a second cylindrical portion 133 positioned at proximal end 126 of housing 122 and having an outer diameter greater than the outer diameter of first cylindrical portion 129. A plurality of gripping ribs 135 also radially outwardly extend on second cylindrical portion 133 and are aligned with longitudinal access of body 18.

Housing 122 also has an interior surface 130 defining a recessed chamber 132 opened at distal end 124. An annular second compression lip 137 radially, inwardly extends from interior surface 130 and has an inner diameter slightly smaller than the outer diameter of first compression ring 55. Positioned proximal of second compression ring 137 on interior surface 130 are second engagement threads 134 configured for rotational, threaded engagement with first engagement threads 57 on proximal end 24 of body 18.

Rotation nut 48 further comprises a tubular shaft 136 distally projecting from proximal end wall 128 within recess chamber 132 of housing 122. Shaft 136 extends to a distal end 145 having a distal end face 146. Shaft 136 also has an exterior surface 138 having an outer diameter and an interior surface 140 defining an entryway 142 longitudinally extending through shaft 136 and proximal end wall 128. Interior surface 140 radially outwardly expands at proximal end 126 of housing 122 to form an enlarged receiving mouth 144.

An annular second ridge 148 distally projects from distal end face 146 of shaft 136 and encircles entryway 142 extending through shaft 136. Second ridge 148 is defined by an annular distal end face 150 and an annular outer sidewall 152. Outer sidewall 152 has an outer diameter smaller than the inner diameter of compression chamber 58. Accordingly, a second receiving groove 149 is formed between outside wall 152 of second ridge 148 and interior surface 60 of compression chamber 58 when shaft 136 is received within compression chamber 58.

In the assembled condition, as shown in FIG. 4, rotation nut 48 is configured so that shaft 136 can be received within compression chamber 58 while, simultaneously, proximal end 24 of body 18 is received within recess chamber 132 of rotation nut 48. As shaft 136 is advanced within compression chamber 58, first compression lip 55 having an outer diameter slightly larger than the inner diameter of second compression lip 137 becomes biased against second compression lip 137. As additional force is applied, second compression lip 137 and distal end 124 radially outwardly expand to allow first compression lip 55 to pass through second compression lip 137. Once this is accomplished, second compression lip 137 returns to its original configuration behind first compression lip 55, thereby holding proximal end 24 of body 18 within recess 132 of rotation nut 48. In this position, first engagement threads 57 on proximal end 24 of body 18 are biased against second engagement threads 134 positioned on interior surface 130 of housing 122. First engagement threads are configured to complementarily engage second engagement threads 134 when rotation nut 48 is rotated relative to body 18. The rotational engagement between first engagement threads 57 and second engagement threads 134 causes shaft 136 to advance within compression chamber 58.

Furthermore, as shaft 136 is advanced within compression chamber 58, distal end 145 of shaft 136 is mated with second ring 115 of slip ring 50. More specifically, annular second ridge 148 at distal end 145 of shaft 136 is received within second access 120 of slip ring 50 and second ring 115 of slip ring 50 is received within second receiving groove 149 of shaft 136. In the position as shown in FIG. 4, lumen 66 in body 18, passageway 90 in seal 52, opening 109 in slip ring 50, and entryway 142 in shaft 136 are each axially aligned and communicating with each other to allow passage 56 to extend therethrough.

To block off passage 56, rotation nut 48 is rotated relative to body 18 causing shaft 136 to advance within compression chamber 58 as a result of the engagement between first engagement threads 57 and second engagement threads 134. As shaft 136 advances, seal 52 is compressed between shoulder 72 of body 18 and slip ring 50. The compression of seal 52 causes interior surface 88 of seal 52 to radially project inward, thereby constricting passageway 90 extending through seal 52. As depicted in FIG. 5, shaft 136 continues to advance until interior surface 88 of seal 52 presses together completely closing and sealing passageway 90 through seal 52. Simultaneously, seal 52 radially, outwardly compresses against interior surface 60 of compression chamber 50 so as to form a seal therebetween. In this position, a distal portion 154 slightly extends within lumen 66 while a proximal portion 156 slightly projects within opening 109 of slip ring 50.

In an alternative use, as shown in FIG. 5A, an elongated member 28, such as a catheter or guidewire, can be longitudinally disposed through passage 56 for insertion within the cardiovascular system of a patient, as discussed with regard to FIG. 1. When elongated member 28 is so used, shaft 136 can be selectively advanced within compression chamber 58 until interior surface 88 of seal 52 constricts to press and seal around an exterior surface 29 of elongated member 28. By selectively advancing or retracting shaft 136, the amount of pressure applied by seal 52 on elongated member 28 can be selectively controlled. As such, elongated member 28 can be advanced or retracted within passage 56 while maintaining a seal around elongated member 28 that prevents leakage of blood or other fluids back flowing through lumen 66.

Seal 52 is preferably made from a deformable, resilient material which allows seal 52 to compress and either independently seal or seal around a member positioned therethrough. The material should also enable seal 52 to independently conform back to its original configuration as shaft 136 is retracted from compression chamber 58. The preferred material for seal 52 is silicone, however, other kinds of conventional rubbers can also be used.

The function of slip ring 50 is to prevent the twisting of seal 52 as shaft 136 is advanced within compression chamber 58. That is, as shaft 136 is advanced during annular rotation, distal end face 146 of shaft 136 slips against slip ring 50, thereby preventing transfer of this annular rotation to seal 52 which could twist seal 52. Twisting of seal 52 can cause seal 52 to apply a counter rotating force to shaft 136 which, if sufficient, can independently back-off or unscrew shaft 136 from within compression chamber 58, thereby opening seal 52 and possibly causing fluid leakage thereat.

To help insure rotational slippage between shaft 136 and slip ring 50, slip ring 50 is preferably made from a relatively rigid material having a relatively low coefficient of friction such as polytetrafluoroethylene, more commonly known as Teflon®. To assist in rotational slipping between shaft 136 and slip ring 50, and to provide a smoother interaction between the components within valve assembly 26, a small quantity of oil or other lubricant, such as a medical grade silicone oil, can be used to lubricate the interactive components of valve assembly 26. Seal 52, and more specifically interior surface 88 of seal 52, is also preferably coated with an oil. The oil helps prevent interior surface 88 of seal 52 from sticking together as shaft 136 is retracted from within compression chamber 58 to open passageway 90 through seal 52.

In an alternative embodiment, as shown in FIG. 5B, valve assembly 26 can be configured without the use of slip ring 50. In this embodiment, annular second ridge 148 on shaft 136 is received within second recess 106 of seal 52 while simultaneously annular second tongue 100 is received within second receiving groove 149 on shaft 136. In this embodiment, however, it is preferred that shaft 136 and seal 52 have a relationship which permits shaft 136 to advance under rotation without twisting or rotating seal 52. This can be accomplished by either the addition of lubricants or by forming seal 52 out of a material having a relatively low coefficient of friction.

In preferred embodiment, body 18 and rotation nut 48 are preferably molded from a clear polycarbonate plastic. Such a material allows for easy molding, moderate flexibility, and visualizing of the internal components and operation of adapter 16. Of course, alternative types of conventional plastics can also be used.

In one embodiment of the present invention, means are provided for coupling shaft 136 to body 18 and for selectively advancing shaft 136 into compression chamber 58 so as to compress and deform seal 52 within compression chamber 58. By way of example and not by limitation, the means for coupling and advancing includes first engagement threads 57 positioned on exterior surface 19 at proximal end 24 of body 18 and second engagement threads 134 positioned on interior surface 130 of housing 122. As previously discussed with regard to FIGS. 3–5, as shaft 136 is advanced within compression chamber 58, rotational engagement between first engagement threads 57 and second engagement threads 134 couples shaft 136 to body 18. Furthermore, rotation of shaft 136 relative to body 18 causes shaft 136 to advance within compression chamber 58 to compress and deform seal 52 within compression chamber 58.

Of course, the present invention also envisions using all other comparable configurations or alternative types of coupling and advancing. By way of example and not by limitation, first engagement threads 57 could be positioned on interior surface 60 of compression chamber 58 while second engagement threads 134 are complementarily positioned on exterior surface 138 of shaft 136 for coupling and advancing shaft 136 within compression chamber 58. Alternatively, complementary sets of barbs or ridges could replace first engagement threads 57 and second engagement threads 134. As shaft 136 is advanced within compression chamber 58, the complementary sets of barbs or ridges can mechanically interact to couple shaft 136 to body 18.

The present invention also provides means for interlocking distal end 85 of seal 52 with annular shoulder 72 of body 18. The interlocking is used to prevent seal 52 from becoming displaced or misoriented within compression chamber 58. More specifically, the interlocking is used to prevent seal 52 from sticking within lumen 66 after seal 52 is compressed within compression chamber 58. By way of example and not by limitation and as discussed above with regard to FIGS. 3–5, the above means for interlocking distal end 85 of seal 52 comprises annular first ridge 74 projecting from shoulder 72 of body 18 to form first receiving groove 80 positioned between first ridge 74 and interior surface 62 of compression chamber 58. The above interlocking means also comprises annular first tongue 92 distally projecting from distal end face 86 of seal 52 and defining first recess 98.

As discussed with regard to FIG. 4, as seal 52 is received within compression chamber 58, first tongue 92 is received within first receiving groove 80 and annular first ridge 74 is received within first recess 98. In this configuration, distal end 85 of seal 52 is interlocked with shoulder 72 since, during compression of seal 52, first tongue 92 is held within first receiving groove 80 and prevented by first ridge 74 from slipping or flowing into lumen 66. Use of this interlocking configuration significantly prevents seal 52 from sticking within lumen 66 after seal 52 has been compressed within compression chamber 58.

Of course, the present invention also envisions all equivalent configurations for interlocking distal end 85 of seal 52 with shoulder 72. By way of example and not by limitation, in contrast to first tongue 92 having an annular configuration, first tongue 92 could comprise one or more individual fingers distally projecting from proximal end face 86 of seal 52. Likewise, annular first receiving groove 80 could be configured to correspond to one or more individual receiving slots for receiving the individual fingers.

The present invention also provides means for interlocking proximal end 83 of seal 52 with distal end 145 of shaft 136. The interlocking is used to prevent displacement or misalignment of seal 52 within compression chamber 58. More specifically, the interlocking is used to prevent seal 52 from sticking within entryway 142 of shaft 136 after seal 52 is compressed within compression chamber 58. As discussed with regard to FIGS. 3 and 4, the means for interlocking proximal end 83 of seal 52 includes annular second tongue 100 proximally projecting from proximal end face 84 of seal 52 and defining second recess 106. The interlocking means further includes annular second ridge 148 distally projecting from distal end face 146 of shaft 136 and defining second receiving groove 149.

As discussed with regard to FIG. 5B, second ridge 148 can be received within second recess 106 and annular second tongue 100 can be received within second receiving groove 149. In this configuration, proximal end 83 of seal 52 is interlocked with distal end 145 of shaft 136 since, during compression of seal 52, second tongue 100 is held within second receiving groove 149 and prevented by second ridge 148 from slipping or flowing into entryway 142.

The means for interlocking proximal end 83 of seal 52 can likewise have the same alternative configurations as discussed with the means for interlocking distal end 85 of seal 52. For example, second tongue 100 can comprise one or more individual fingers proximally projecting from proximal end face 84 of seal 52.

In yet another alternative embodiment, the means for interlocking proximal end 83 of seal 52 can include slip ring 50 being positioned between seal 52 and shaft 136 as discussed with regard to FIGS. 4 and 5. In this embodiment, second ridge 148 is received within second access 120 of slip ring 50 and first ring 108 of slip ring 50 is received within second recess 106 of seal 52, thereby interlocking proximal end 83 of seal 52 with distal end 145 of shaft 136 through slip ring 50. This configuration also prevents second tongue 100 from entering within entryway 142 which could result in seal 52 sticking within entryway 142 of shaft 136 after compression of seal 52 within compression chamber 58.

The present invention also provides means for selectively closing lumen 66 at proximal end 24 of tubular body 18. By way of example and not by limitation, the means for selectively closing includes valve assembly 26, as discussed above, and includes all of the related alternative embodiments as also discussed above.

The present invention also provides means for selectively closing lumen 66 at proximal end 24 of tubular body 18. By way of example and not by limitation, the means for selectively closing includes valve assembly 26 as discussed above and includes each of its alternative embodiments.

Referring again to FIG. 2, rotatable connector 22 positioned at distal end 20 of body 18 is shown in a partial disassembled configuration. As disclosed therein, rotatable connector 22 comprises a retaining flange 158 encircling and radially extending outward from proximal end 20 of body 18. Rotatable connector 22 also includes an annular cap 160 rotatably encircling body 18 proximal of flange 158 and a split ring 162 rotatably encircling body 18 between flange 158 and cap 160. Rotatable connector 22 further comprises a tubular hub 164. The configuration and positioning of the elements of rotatable connector 22 are better shown in FIG. 6 which discloses a cross-sectional fully exploded view of rotatable connector 22.

Figure 6:
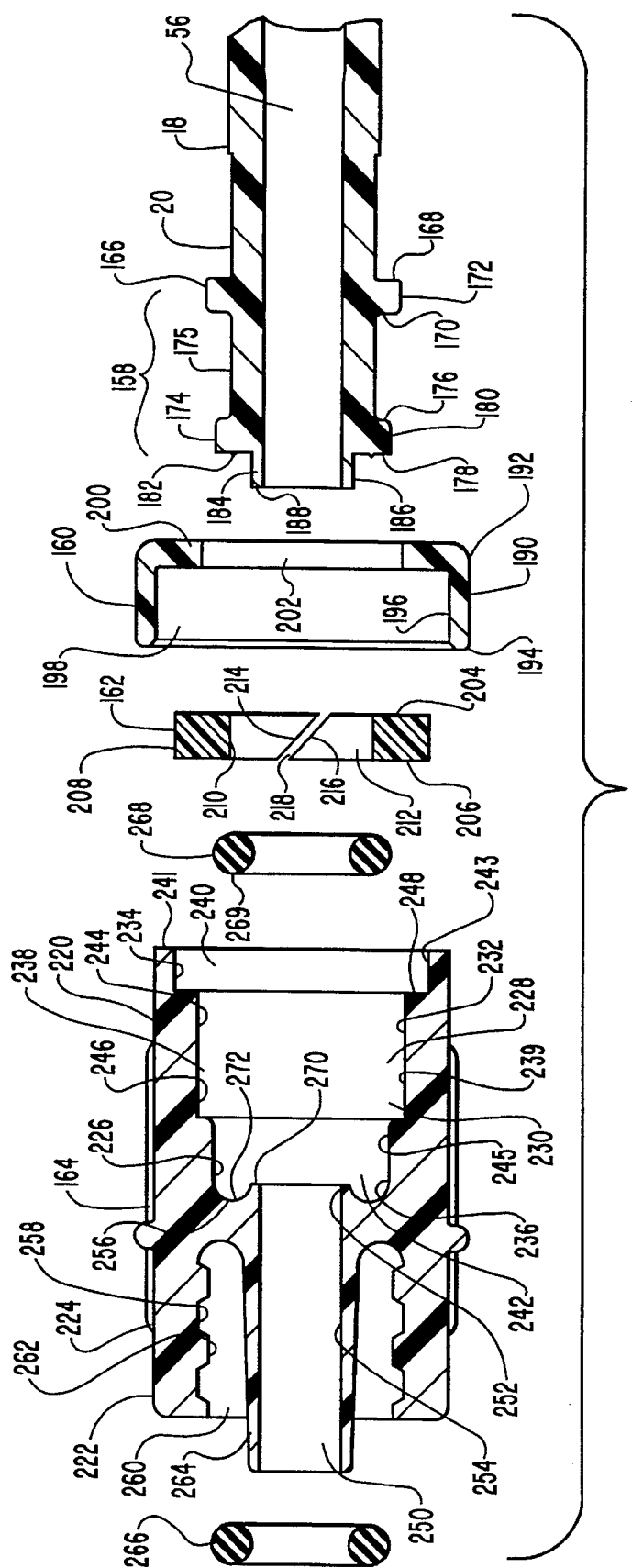
FIG. 6 is an enlarged cross-sectional view of the rotatable connector shown in FIG. 2 in a disassembled condition.

As disclosed in FIG. 6, retaining flange 158 comprises and annular proximal flange 166 encircling and radially extending outward on distal end 20 of body 18. Proximal flange 166 comprises an annular proximal side wall 168, an annular distal side wall 170, and an annular outer surfhce 172. Retaining flange 158 further comprises an annular distal flange 174 encircling and radially extending outward from said distal end 20 of body 18. Distal flange 174 is shown as having an annular proximal side wall 176, an annular distal side wall 178, and an annular outer surface 180. Positioned between proximal flange 166 and distal flange 174 is a cylindrical section 175 having a reduced outer diameter. Of course, in the alternative embodiment retaining flange 158 can be made having a uniform outer diameter along its length. Distally projecting from distal sidewall 178 of distal flange 158 is an annular ridge 182 encircling body 18. Also distally projecting from distal sidewall 178 of distal flange 174 is a cylindrical stem 184 adjacently encircling passage 56 extending through body 18. Stem 18 has an exterior surface 186 and terminates at a distal terminus 188.

Figure 7:
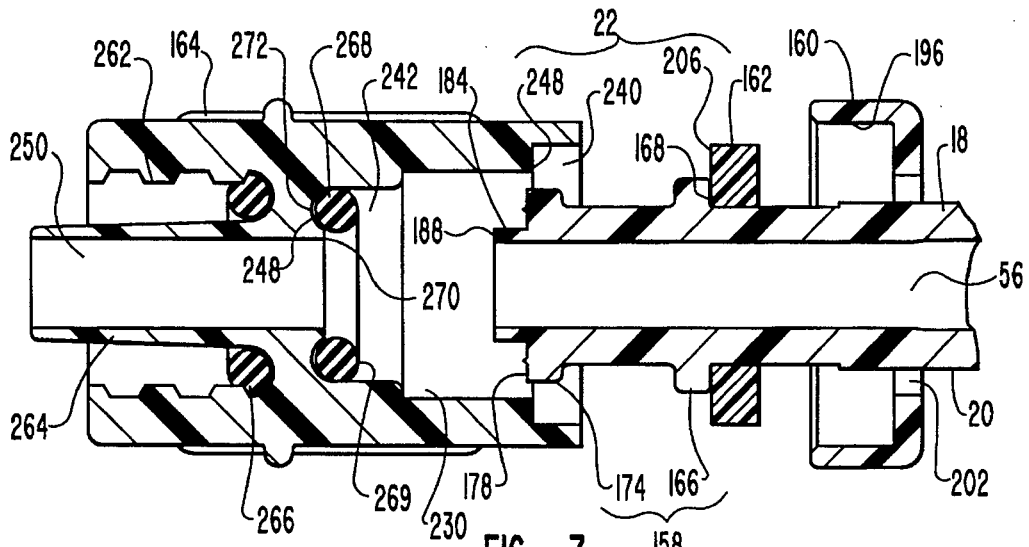
FIG. 7 is a cross-sectional view of the rotatable connector shown in FIG. 6 in a first stage of assembly.

Annular cap 160 is shown in FIG. 6 as comprising an annular sleeve 190 having a proximal end 192 and an opposing distal end 194. Sleeve 190 also has an interior surface 196 having an inner diameter and defining a recess 198. An annular end wall 200 radially extends inward from interior surface 196 of sleeve 190 at a proximal end 192 thereof to define an aperture 202. Aperture 202 has an inner diameter greater than the outer diameter of both proximal flange 166 and distal flange 174. Accordingly, as shown in FIG. 7, distal end 20 of body 18 can be received within aperture 202 of cap 160 so that cap 160 can rotatably encircle body 18 proximal of retaining flange 158.

Referring again to FIG. 6, split ring 162 is shown as comprising an annular proximal end face 204, an annular distal face 206, and an annular outer surface 208 having an outer diameter. Split ring 162 further comprises an interior surface 210 defining an opening 212 having an inner diameter and longitudinally extending therethrough. Split ring 162 is further shown as having a first end 214 adjacent to a second end 216 which define a slit 218. Slit 218 extends between distal end face 206 and proximal end face 204 of split ring 162. Opening 212 through split ring 162 has an inner diameter smaller than the outer diameter of proximal flange 166. However, as a result of slit 218, split ring 162 is capable of radially expanding to enable distal end 20 of body 18 to be received within opening 212 so that split ring 162 can rotatably encircle body 18 between proximal flange 166 and cap 160, as shown in FIG. 7. As used in the specification and the appended claims, reference to the "outer diameter" of split ring 162 and the "inner diameter" of opening 212 through split ring 162 refer to dimensions of split ring 162 in an unexpanded condition. Of course, such dimensions increase as split ring 218 expands as a result of the separation of first end 214 and second end 216.

Tubular hub 164 is disclosed in FIG. 6 as having a proximal end 220, a distal end 222, and an exterior surface 224 with an outer diameter extending therebetween. Hub 164 further includes an interior surface 226 defining a passageway 228 longitudinally extending therethrough. Passageway 228 is shown in FIG. 6 as comprising an access chamber 230 positioned at proximal end 220 of hub 164.

Access chamber 230 is defined by an interior surface 232 extending from a proximal end 234 to a distal end 236 of access chamber 230.

Access chamber 230 is further defined as comprising a transition bore 238, an entrance bore 240, and a sealing bore 242. Transition bore 238 is defined by cylindrical interior surface 239 that extends between a proximal end 244 and a distal end 246. Entrance bore 242 has an inner diameter greater than the inner diameter of transition bore 238 and is defined by cylindrical interior surface 243 that extends from a proximal terminus 241 of hub 164 to proximal end 244 of transition bore 238. An annular shoulder 248 extends between proximal end 244 of transition bore 238 and entrance bore 240. Sealing bore 242 has an inner diameter smaller than the inner diameter of transition bore 238 and is defined by cylindrical interior surface 245 that extends from distal end 246 of transition bore 238 to distal end 236 of access chamber 230.

In addition to access chamber 230, passageway 228 also includes a transfer duct 250 having a proximal end 252 concentric with distal end 236 of access chamber 230. Transfer duct 250 is defined by an interior surface 254 having an inner diameter smaller than the inner diameter of access chamber 230. As such, a shoulder 256 extends between proximal end 252 of transfer duct 250 and distal end 236 of access chamber 230.

Distal end 222 of hub 164 is also shown as having an interior surface 258 defining a receiving slot 260 and having a set of engagement threads 262 positioned thereon. Engagement threads 262 are preferably configured for a conventional luer lock attachment. However, alternative types of threads can also be used. Distally projecting from shoulder 256 within hub 164 is a tubular stem 264 having interior surface 254 with transfer duct 250 extending therethrough as previously discussed. A seal ring 266 is shown in FIG. 6 for positioning within receiving slot 260 proximal of engagement threads 262. As shown in FIG. 7, seal ring 266 can then be used for sealing a corresponding connector (not shown) threadedly engaged with engagement threads 262.

In a similar fashion, FIG. 6 also discloses a seal ring 268 having an exterior surface 269 configured to be biased against shoulder 248 and encircling transfer duct 250. As shown in FIG. 6, shoulder 248 includes an annular mouth 270 encircling transfer duct 250 and positioned adjacent thereto. Shoulder 248 further includes a grooved face 272 positioned between annual mouth 270 and interior surface 232 of access chamber 230. Grooved face 272 has a configuration complimentary to exterior surface 269 of seal ring 268 so as to produce a complementary fit therebetween as shown in FIG. 7.

Figure 8:
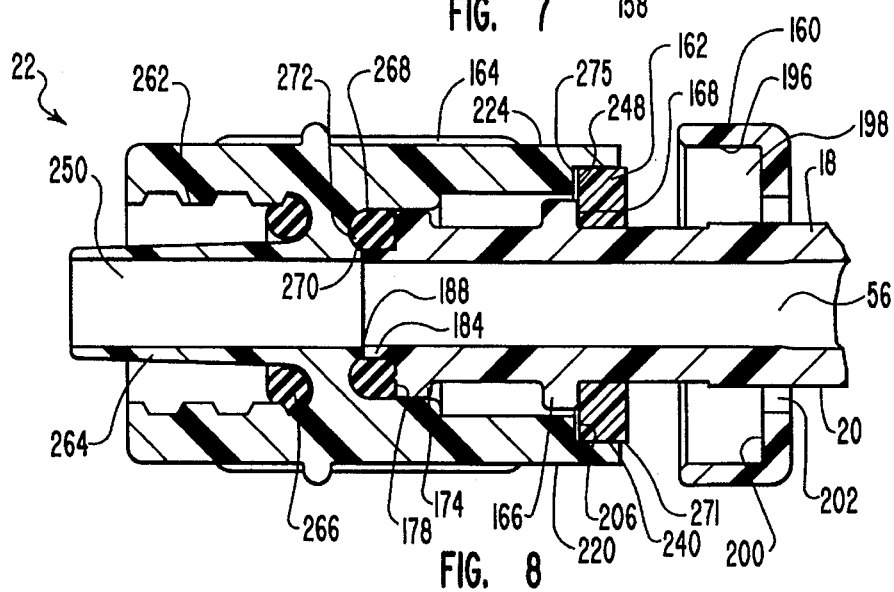
FIG. 8 is a cross-sectional view of the rotatable connector of FIG. 6 in a second stage of assembly.
Figure 9:
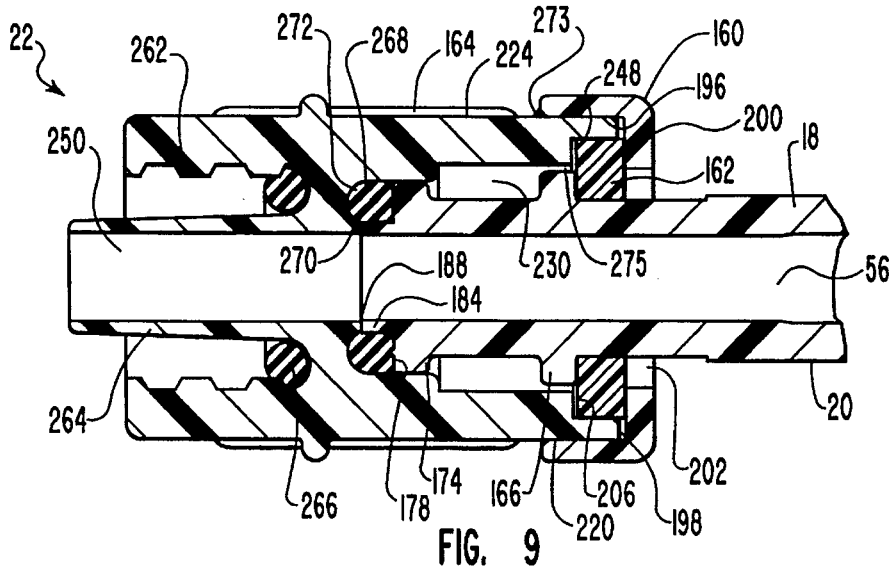
FIG. 9 is a cross-sectional view of the rotatable connector of FIG. 6 in a fully assembled condition.

As shown in FIGS. 7–9, assembly of rotatable connector 22 is a multi-step process. In the first step as shown in FIG. 7, split ring 162 and cap 160 are positioned to rotatably encircle body 18 proximal of retaining flange 158 as previously discussed. Likewise, seal ring 268 is positioned within access chamber 230 so as to be biased against grooved face 272 of shoulder 248. In this position, distal end 20 of body 18 is advanced within access chamber 230, until distal sidewall 178 of distal flange 174 is biased against seal ring 268.

As shown in FIG. 8, distal end 20 of body 18 is preferably configured to mate with access chamber 230 so as to produce an airless seal between transfer duct 250 in hub 164 and passage 56 in body 18. To this end, distal flange 174 is sized to snugly be received within sealing bore 142 and distal stem 184 is sized to snugly be received within seal 268. As distal sidewall 178 of distal flange 174 compresses against seal ring 268, seal ring 268 deforms to fill all surrounding space and in so doing presses the air therefrom. In the final position, distal terminus 188 of distal stem 184 is biased against annular mouth 270 of shoulder 248, thereby completely bounding seal ring 268 in a substantially airless enclosure. As a result of forming an airless seal between transfer duct 250 in hub 164 and passage 56 in body 18, the chance of air bubbles entering the blood stream at the point of the airless seal is decreased.

FIG. 8 also discloses split ring 162 being received within entrance bore 240 so that distal end face 206 of split ring 162 is biased against proximal sidewall 168 of proximal flange 166. This configuration urges distal sidewall 178 of distal flange 174 against seal ring 268, thereby maintaining the airless seal discussed above.

As shown in FIGS. 8 and 9, cap 160 has an inner diameter larger than the outer diameter of hub 164. Accordingly, as cap 160 and hub 164 are pressed together, proximal end 220 of hub 164 is received within recess 198 of cap 160. Furthermore, split ring 162 is shown positioned so as to have an exposed portion 271 proximally projecting from entrance bore 240 of hub 164 and a gap 275 positioned between end face 206 of split ring 162 and shoulder 248 of hub 164. Accordingly, as cap 160 and hub 164 are pressed together, end well 200 of cap 160 produces a positive compression force against split ring 162. In turn, split ring 162 produces a positive compression force against proximal flange 166 as discussed above. In this configuration, as shown in FIG. 9, an adhesive 273 is applied between the interior surface 196 of cap 160 and exterior surface 220 of hub 164 so as to rigidly secure cap 160 to hub 164.

The preferred adhesive for connecting cap 160 to hub 164 is a conventional ultraviolet adhesive. After hub 164 is received within recess 198 of cap 160, a small amount of adhesive 273 is positioned at distal end 194 of cap 160 at the intersection of cap 160 and hub 164. Adhesive 273 then wicks around hub 164 and between interior surface 196 of cap 160 and exterior surface 224 of hub 164. Ultraviolet light is then directed onto rotatable connector 22 which then immediately sets adhesive 273. Of course, alternative types of adhesives can also be used. Once cap 160 is secured in place, split ring 162 is continually urged against proximal flange 168 so as to maintain the airless seal between passage 56 of body 18 and transfer duct 250 of hub 164. Furthermore, the attachment of cap 160 to hub 164 prevents separation of body 18 and hub 164 but allows both hub 164 and cap 160 to annularly rotate relative to body 18.

During rotation of hub 164 relative to body 18, split ring 162 and seal ring 268 typically rotate with hub 164. Slip surfaces are thus formed between distal end face 206 of split ring 162 and proximal sidewall 168 of proximal flange 166 and between distal sidewall 178 of distal flange 174 and seal ring 268. The ease at which hub 164 rotates relative to body 18 can thus be varied by the material used for split ring 167 and seal ring 268.

Split ring 162 is preferably made from a material having a low coefficient of friction such as polytetrafluoroethylene so as to allow easy and smooth rotation of hub 164 relative to body 18. Split ring 162 can alternatively be made of materials having different coefficients of friction such as acetal plastic. Seal ring 268 is preferably made from silicone. Alternatively, seal ring 268 can be made of other materials having varied coefficients of friction. By way of example and not by limitation, seal ring 268 can be made from natural rubber, ethylene propylene, and fluorosilicone.

The ease at which hub 164 rotates relative to body 18 is also a function of the amount of force used in applying cap 160 onto hub 164. That is, by increasing the force in pressing cap 160 and hub 164 together, the friction between the above discussed slip surfaces is also increased, thereby making it more difficult to rotate 164 relative to body 18.

The present invention also provides means for connecting distal end 20 of tubular body 18 to a medical device, such as introducer 12, used in fluid communication with the body of patient 10. By way of example and not by limitation, the means for connecting comprises rotatable connector 22, as disclosed above, and includes all of the alternative embodiments as discussed therewith.

Figure 10:
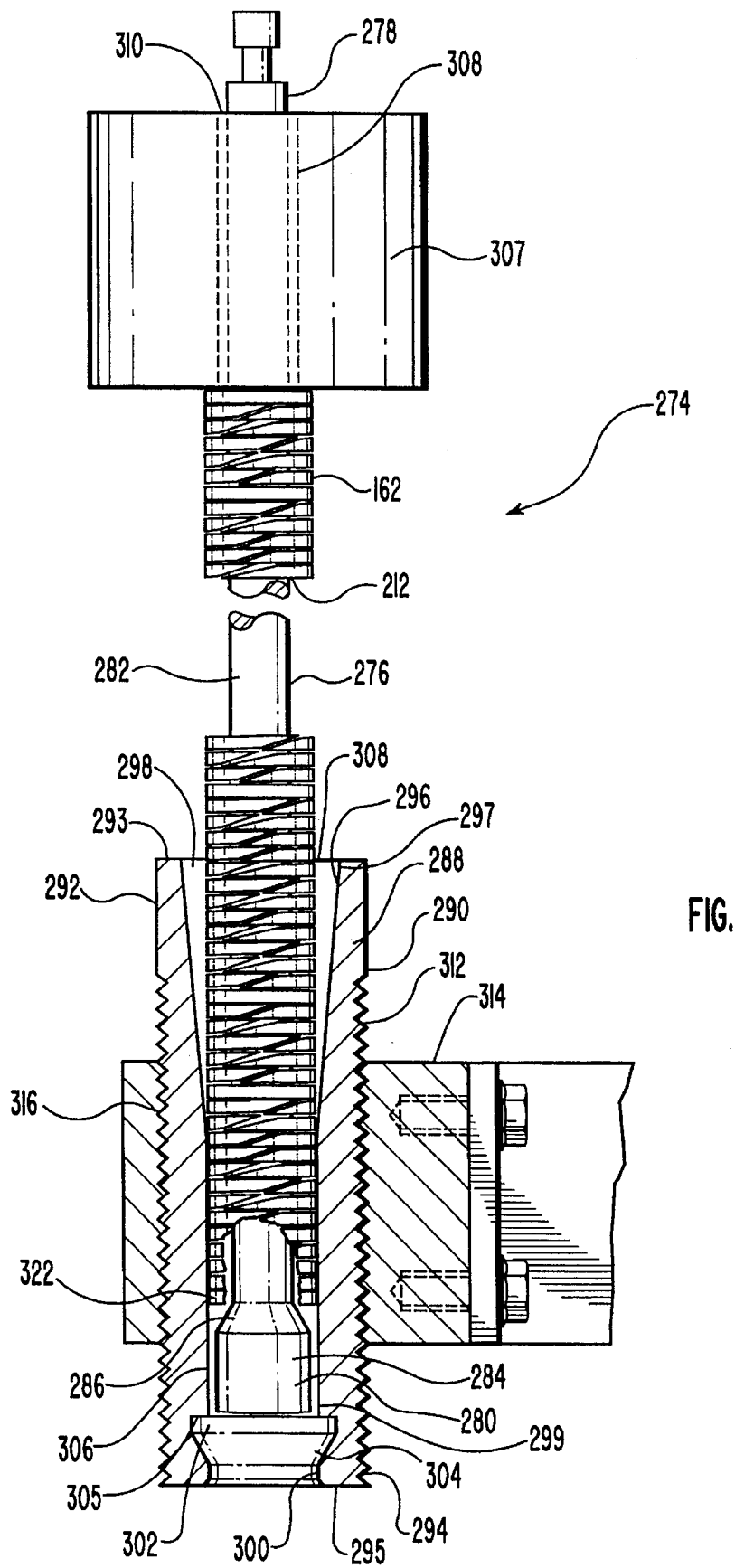
FIG. 10 is a plan view of a positioning apparatus used for attaching a slip ring onto the distal end of the adapter, as shown in FIG. 6.

The attachment of split ring 162 onto body 18 proximal of retaining flange 158 is preferably accomplished through the use of a positioning apparatus 274 as shown in FIG. 10. Positioning apparatus 274 includes a rigid, substantially cylindrical shaft 276 having a top end 278 and a bottom end 280. Shaft 276 is shown as comprising a retaining shaft 282 positioned at top end 278 and having an outer diameter smaller than the inner diameter of split ring 162. An expansion shaft 284 is positioned at bottom end 280 and has an outer diameter larger than the inner diameter of split ring 162. Finally, a frustoconical transition shaft 286 extends between retaining shaft 282 and expansion shaft 280.

Positioning apparatus 274 further comprises a housing 288 having an exterior surface 290 extending between a top end 292 and a bottom end 294. Positioned at top end 292 is a top end face 293 and positioned at bottom end 294 is a bottom end face 295. Housing 288 further includes an interior surface 296 defining a passageway 298 extending therethrough. Interior surface 296 defines a plurality of differently configured sections. Positioned at top end 292 of housing 288 is a cylindrical first surface 306 having an inner diameter substantially equal to the outer diameter of split ring 162 and extending between a first end 297 and a second end 299. Near top end 292, first surface 306 gradually radially expands outward so as to form an enlarged receiving mouth 308 at top end face 293.

A cylindrical second surface 302 is aligned with and positioned adjacent to second end 299 of first surface 306. Second surface 302 has an inner diameter larger than the inner diameter of first surface 306. Extending between first surface 306 at second end 299 and second surface 302 is an annular shoulder 305. A cylindrical third surface 300 is positioned at bottom end 294 of housing 288. Third surface 300 has an inner diameter substantially equal to the outer diameter of split ring 162. A frustoconical constriction surface 304 extends between second surface 302 and third surface 300.

To attach split ring 162 onto body 18, initially bottom end 280 of shaft 276 is received within cylindrical first surface 306 and top end 278 of shaft 276 is received within opening 212 of a plurality of split rings 162. The split rings 162 thus encircle shaft 276 as shown in FIG. 10.

The present invention provides means for urging split ring 162 received on retaining shaft 282 against transition shaft 286 of shaft 276. By way of example and not by limitation, a weight 307 is provided having an interior surface 308 defining a channel 310 longitudinally extending therethrough. Channel 310 has an inside diameter larger than the outer diameter of retaining shaft 282 but smaller than the outer diameter of split ring 162. Top end 271 of retaining shaft 282 is received within channel 310 so that weight 307 encircles retaining shaft 282.

Weight 307 provides a gravitational force that pushes split rings 162 down the length of retaining shaft 282 and towards transition shaft 286. Split rings 162, however, are held in place by the fact that a split ring 322 at bottom end 280 is unable to expand over transition shaft 286 because interior surface 296 of cylindrical first surface 306 is comparable to the outside diameter of split rings 322. Weight 307 also has an outer diameter which can either be larger than or smaller than the inner diameter of first surface 306. Of course, other types of mechanical or manual forces could be applied to split rings 162 to push split rings 162 toward transition shaft 286.

Means are also provided for moving housing 290 relative to shaft 276. Preferably, this is accomplished between a first position and a second position. By way of example and not by limitation, housing 288 is shown having a plurality of threads 312 positioned on exterior surface 290. A clamp 314 having complementary threads 316 mechanically engages housing 288 by thread connection between threads 312 on housing 288 and threads 316 on clamp 314. Clamp 314 can then be attached to a piston or any other kind of mechanical or manual device which permits housing 288 to move along a longitudinal access of shaft 276. In the preferred embodiment, shaft 276 is held stationary by being clamped at top end 278.

Figure 13:
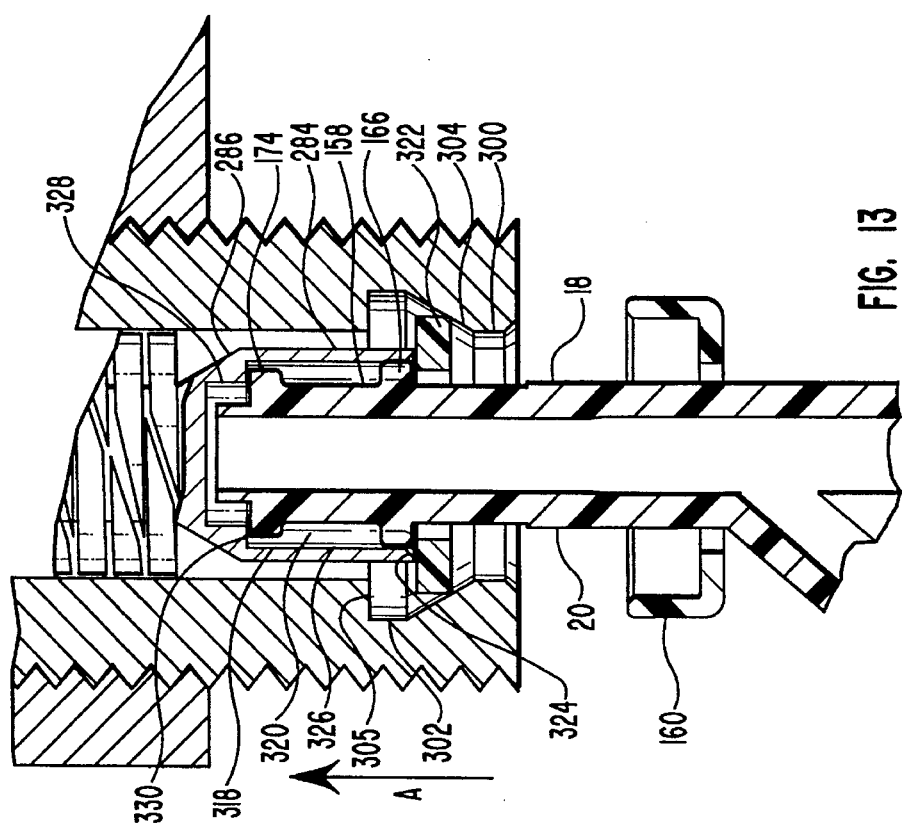
FIG. 13 is an enlarged cross-sectional view of the positioning apparatus compressing the split ring around the distal end of the adapter and proximal to the flange.

As best shown in FIG. 13, expansion shaft 284 also includes an interior surface 318 defining a recess 320. Recess 320 is opened at bottom end face 324 of expansion shaft 284 and is configured to receive retaining flange 158 positioned on distal end 20 of body 18. Interior surface 318 is shown as comprising a substantially cylindrical first poaion 326 positioned at bottom end face 324 of expansion shaft 284. A substantially cylindrical second portion 328 is axially aligned with first portion 326 and extends towards top end 278 of shaft 276. First portion 326 has an inner diameter larger than the outer diameter of retaining flange 158. Second portion 328 has an inner diameter smaller than the outer diameter of retaining flange 158. Accordingly, as distal end 20 of tubular body 18 is advanced within recess 320, distal flange 174 of retaining flange 158 becomes biased against an annular shoulder 330 extending between first portion 326 and second portion 328.

Figure 11:
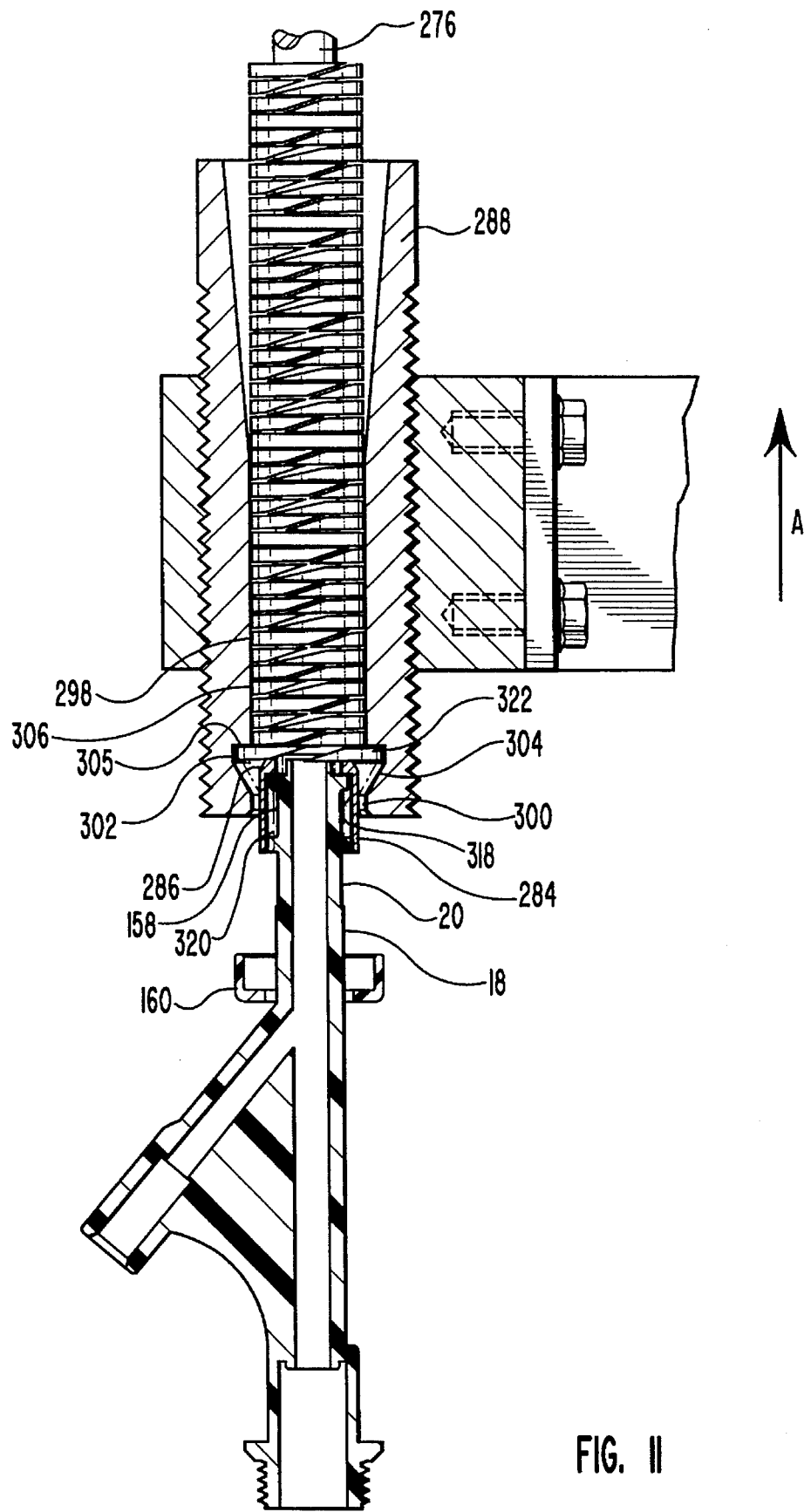
FIG. 11 is a partial cross-sectional plan view of the positioning apparatus in a first stage for positioning a split ring on the distal end of the adapter.

With distal end 20 of body 18 disposed within recess 320, housing 288 begins moving in the direction of arrow A as shown in FIG. 11. At the stage shown in FIG. 11, a sufficient portion of transition shaft 286 of shaft 276 is extending out of cylindrical first surface 306 of housing 288 to cause first split ring 322, under the force of weight 307, to press out of cylindrical first surface 306 and expand over transition shaft 286 into cylindrical second surface 302 of housing 288.

Figure 12:
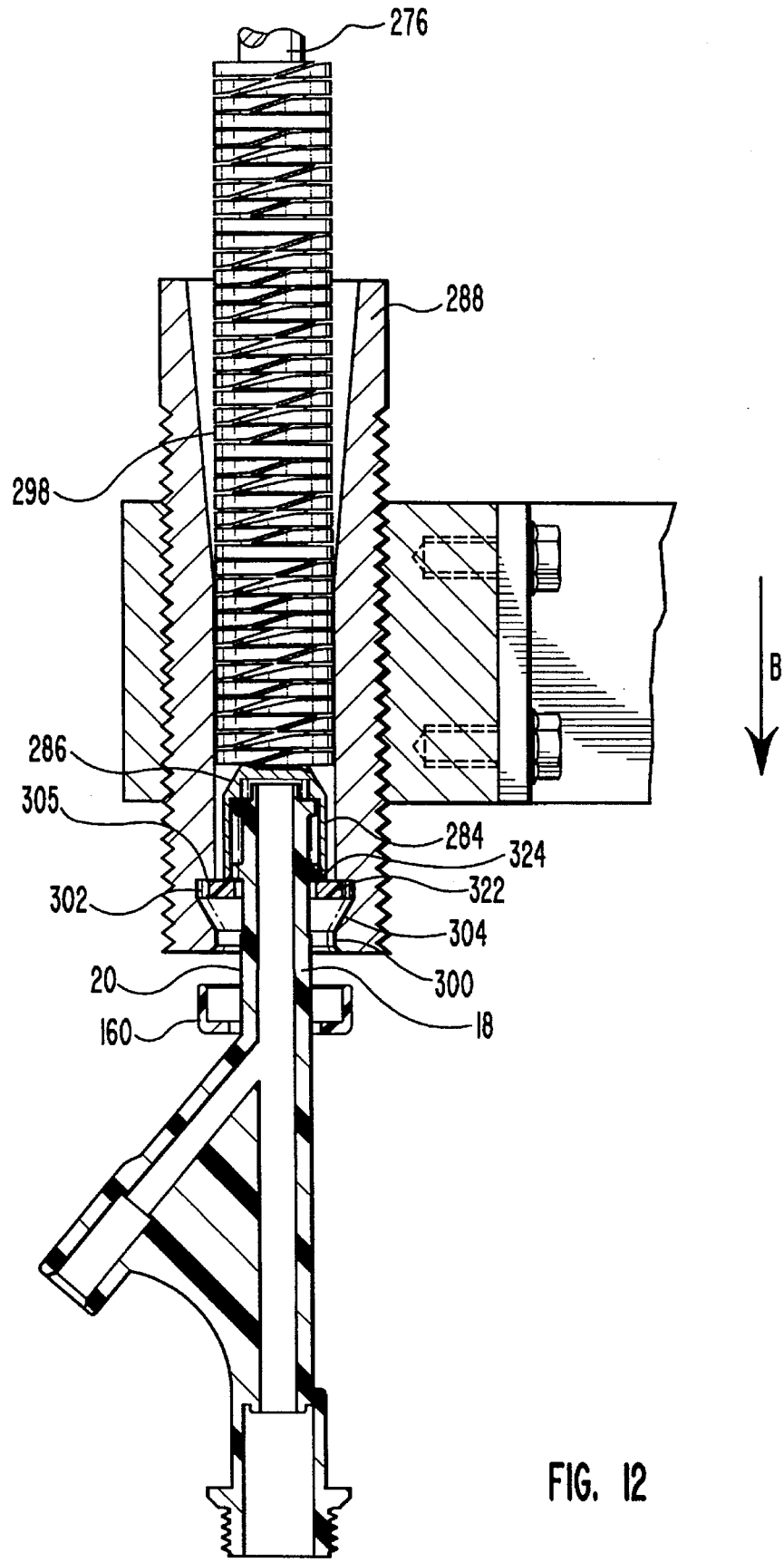
FIG. 12 is a partial cross-sectional plan view of the positioning apparatus having the split ring positioned proximal of the flange on the distal end of the adapter.

Once split ring 322 is positioned within cylindrical second surface 302, housing 288 begins moving in the direction of arrow B as shown in FIG. 12. By so doing, first split ring 322 is engaged by shoulder 305 so as to expand and pass over expansion shaft 284. After first split ring 322 completely passes over expansion shaft 284 so as to encircle body 18 proximal of retaining flange 158, split ring 322 partially self-constricts around body 18 so as to be aligned with bottom and face 324 of expansion shaft 284.

Figure 14:
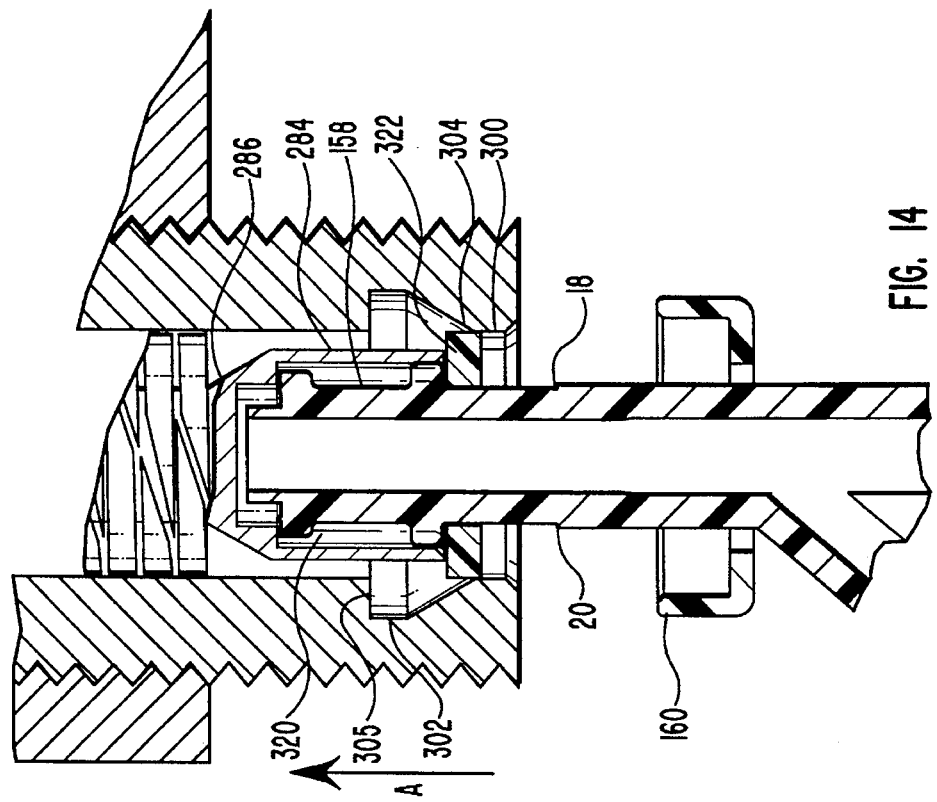
FIG. 14 is a cross-sectional view of the positioning apparatus having the split ring securely positioned on the distal end of the adapter.

Depicted in FIG. 13, housing 288 then begins to travel in the direction of arrow A. As housing 288 does so, bottom end face 324, and at times proximal flange 166, holds split ring 322 in position while constriction surface 304 and third surface 300 of housing 288 radially inwardly compress first split ring 322 so as to snugly fit around body 18 as shown in FIG. 14. Distal end 20 of body 18 having first split ring 322 encircling body 18 proximal of retaining flange 158 can then be removed from recess 320 for subsequent attachment of a different split ring to a different body.

In an alternative embodiment, cylindrical third surface 300, cylindrical second surface 302, and constriction surface 304 can be removed from passage 298. Accordingly, in this embodiment passageway 298 exclusively defines cylindrical first surface 306 extending from top end 292 to bottom end 294 of housing 288. During operation, bottom end face 295. as shown in FIG. 11, acts like shoulder 305 to position split ring 322 around body 18 as discussed above. In this embodiment, however, split ring 322 is not subsequently compressed around body 18 by housing 288. Of course, alternative embodiments can be used to compress split ring 322 around body 18.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for manufacturing a rotatable connector for attachment to a medical device, the method comprising the steps of:
   (a) obtaining a tubular body having a distal end, an exterior surface, and an interior surface defining a passage longitudinally extending therethrough, said tubular body having an enlarged retaining flange with an outer diameter positioned at said distal end and extending radially outward from said exterior surface of said tubular body;
   (b) advancing said distal end of said tubular body throuqh an aperture in an annular cap until said cap is positioned proximal of said retaining flange, said aperture of said cap having an inner diameter larger than said outer diameter of said retaining flange;
   (c) positioning an expandable, annular split ring around said tubular body between said annular cap and said retaining flange, said split ring having an interior surface encircling said tubular body and defining an opening having an inner diameter smaller than said outer diameter of said retaining flange, said split ring also having an outer diameter larger than said inner diameter of said aperture of said cap;
   (d) receiving said distal end of said tubular body within an access chamber positioned at a proximal end of a tubular hub so as to place said distal end of the tubular body and said tubular hub in contact with one another and so as to rotatably fluid couple said passage of said tubular body with a transfer duct communicating with said access chamber thereby forminq a continuous passaqeway with said passaqe and transfer duct; and
   (e) securing said cap to said proximal end of said tubular hub so that said hub and cap are concurrently rotatable about said tubular body.

2. A method as recited in claim 1, wherein said advancing step further comprises said cap having:
   (a) an annular sleeve having a proximal end, a distal end, and an interior surface defining a recess; and
   (b) an annular end wall radially extending inward from said interior surface of sleeve at said proximal end to define said aperture.

3. A method as recited in claim 2, wherein said receiving step further comprises disposing said proximal end of said tubular hub within said recess of said annular sleeve.

4. A method as recited in claim 3, wherein said securing step further comprises adhering said interior surface of said sleeve against said exterior surface of said hub.

5. A method as recited in claim 1, wherein said securing step further comprises locating an ultraviolet adhesive between said cap and said hub.

6. A method as recited in claim 5, further comprising the step of applying ultraviolet light to said ultraviolet adhesive.

7. A method as recited in claim 1, wherein said receiving step further comprises inserting said retaining flange within said access chamber.

8. A method as recited in claim 7, wherein said receiving step further comprises placing at least a portion of said split ring within said access chamber.

9. A method as recited in claim 8, wherein said receiving step further comprises biasing said split ring against said retaining flange so an exposed portion of said split ring proximally projects out of said access chamber.

10. A method as recited in claim 9, wherein said securing step further comprises urging said cap against said exposed portion of said split ring so as to urge said distal end of said tubular body within said access chamber.

11. A method as recited in claim 1, wherein said receiving step further comprises said rotatable connector further having an annular shoulder extending between said proximal end of said transfer duct and said distal end of said access chamber.

12. A method as recited in claim 11, wherein said receiving step further comprises housing a seal ring within said access chamber between said shoulder and said retaining flange.

13. A method as recited in claim 1, wherein said receiving step further comprises said hub having a distal end with a luer lock connection attached thereto.

(e) rotatably fluid coupling said passage of said tubular body with a transtar duct communicating with said access chamber at said distal end of said access chamber, said transfer duct having an inner diameter smaller than said inner diameter of said access chamber;
   (f) inserting said proximal end of said hub within said recess of said cap; and
   (g) securing said cap to said proximal end of said tubular hub so that said hub and cap are concurrently rotatable about said tubular body.

14. A method for manufacturing a rotatable connector for attachment to a medical device, the method comprising the steps of:
   (a) obtaining a tubular body having a distal end, an exterior surface, and an interior surface defining a passage longitudinally extending therethrough, said tubular body having an enlarged retaining flange with an outer diameter positioned at said distal end and extending radially outward from said exterior surface of said tubular body;
   (b) advancing said distal end of said tubular body throuqh an aperture in an annular cap until said cap is positioned proximal of said retaining flange, said annular cap comprising:
      (i) a cylindrical sleeve having a proximal end, a distal end, and an interior surface defining a recess; and
      (ii) an annular end wall radially extending inward from said interior surface of said sleeve at said proximal end to define an aperture, said aperture having an inner diameter larger than said outer diameter of said retaining flange;
   (c) positioning an expandable, annular split ring around said tubular body between said annular cap and said retaining flange, said split ring having an interior surface encircling said tubular body and defining an opening having an inner diameter smaller than said outer diameter of said retaining flange, said split ring also having an outer diameter larger than said inner diameter of said aperture of said cap;

(d) receiving said distal end of said tubular body within an access chamber positioned at a proximal end of a tubular hub so as to place said distal end of the tubular body said tubular hub in contact with one another, said access chamber having a proximal end, a distal end, and an inner diameter;

(e) rotatably fluid coupling said passage of said tubular body with a transfer duct communicating with said access chamber at said distal end of said access chamber thereby forming a continuous passageway with said passaqe and transfer duct, said transfer duct having an inner diameter smaller than said inner diameter of said access chamber;

(f) inserting said proximal end of said hub within said recess of said cap; and (g) securing said cap to said proximal end of said tubular hub so that said hub and cap are concurrently rotatable about said tubular body.

15. A method as recited in claim 14, wherein said obtaining step further comprises said retaining flange having:

(a) a proximal retaining flange encircling and radially outwardly extending from said tubular body;

(b) a distal retaining flange encircling and radially outwardly extending from said tubular body; and (c) a reduced diameter section extending between said proximal retaining flange and said distal retaining flange.

16. A method as recited in claim 14, wherein said securing step comprises locating an adhesive between said sleeve of said cap and said hub.

17. A method as recited in claim 16, further comprising the step of applying ultraviolet light to said adhesive.

18. A method as recited in claim 14, wherein said positioning step comprises said split ring being made of Teflon®.

19. A method as recited in claim 14, wherein said step of rotatably fluid coupling further comprises an annular shoulder extending between transfer duct and said distal end of said access chamber.

20. A method as recited in claim 19, wherein said step of rotatably fluid coupling comprises housing a seal ring between said shoulder and said retaining flange.

21. A method as recited in claim 20, wherein said step of rotatably fluid coupling further comprises pressing a cylindrical stem distally projecting past said retaining flange through said seal ring so as to be biased against said shoulder and communicating with said transfer duct of said hub.

22. A method as recited in claim 21, wherein said step of rotatably fluid coupling further comprises biasing said retaining flange against said seal ring to form an airless seal between said transfer duct in said hub and said passage in said tubular body.

23. A method as recited in claim 14, wherein said receiving step further comprises placing a portion of said split ring within said access chamber so that an exposed portion of said split ring proximally projects past said proximal end of said hub.

24. A method as recited in claim 23, wherein said inserting step further comprises urging said annular end wall of said cap against said exposed portion of said split ring to urge said split ring against said retaining flange.

25. A method as recited in claim 14, wherein said receiving step further comprises said hub having a distal end with a luer lock connection attached thereto.

26. A method as recited in claim 25, further comprising the step of rotating said hub relative to said tubular body for securing the luer lock connection to the medical device.

* * * * *